United States Patent [19]

Hervé et al.

[11] 4,023,734

[45] May 17, 1977

[54] METHOD AND APPARATUS FOR COMMUNITING MARINE ALGAE AND THE RESULTING PRODUCT

[76] Inventors: Rene A. Hervé, les Tertres, Pluduno, 22130 Plancoet; Daniel L. Rouillier, Beauregard, 35, Saint-Meloir-les-Ondes, both of France

[22] Filed: Oct. 15, 1975

[21] Appl. No.: 622,637

[30] Foreign Application Priority Data

Oct. 18, 1974 France ............................ 74.35162

[52] U.S. Cl. .................................... 241/17; 241/23; 241/DIG. 37

[51] Int. Cl.² .......................................... B02C 23/18

[58] Field of Search .................. 241/17, 19, 20, 23, 241/DIG. 37; 71/16; 47/1.4

[56] References Cited

UNITED STATES PATENTS

| | | | |
|---|---|---|---|
| 1,979,124 | 10/1934 | Tival | 241/DIG. 37 |
| 2,583,697 | 1/1952 | Hendley, Jr. et al. | 241/17 X |
| 3,172,546 | 3/1965 | Schreiner | 241/23 |

*Primary Examiner*—Frank A. Spear, Jr.
*Assistant Examiner*—Ferris H. Lander
*Attorney, Agent, or Firm*—DeLio and Montgomery

[57] ABSTRACT

A method of comminuting fresh algae which consists in carrying out a comminuting operation on said algae at a temperature lower than −20°C. Preferably this temperature lies between the range −30° to −100° C. In carrying out the method it is advantageous for the fresh algae to be frozen at a temperature of less than −20° C before being comminuted. In particular, after being broken down, the algae are comminuted by crushing into the form of a wet paste mix, the mean size of the particles in which is less than 10 micrometers.

The invention also relates to apparatus for carrying out the comminuting operation which comprises a comminuting assembly and cooling means associated therewith to hold the operated temperature within said assembly at a level of −20°C by means of a cooling agent. The invention furthermore extends to the algae product whenever produced by the method and apparatus aforementioned.

5 Claims, 5 Drawing Figures

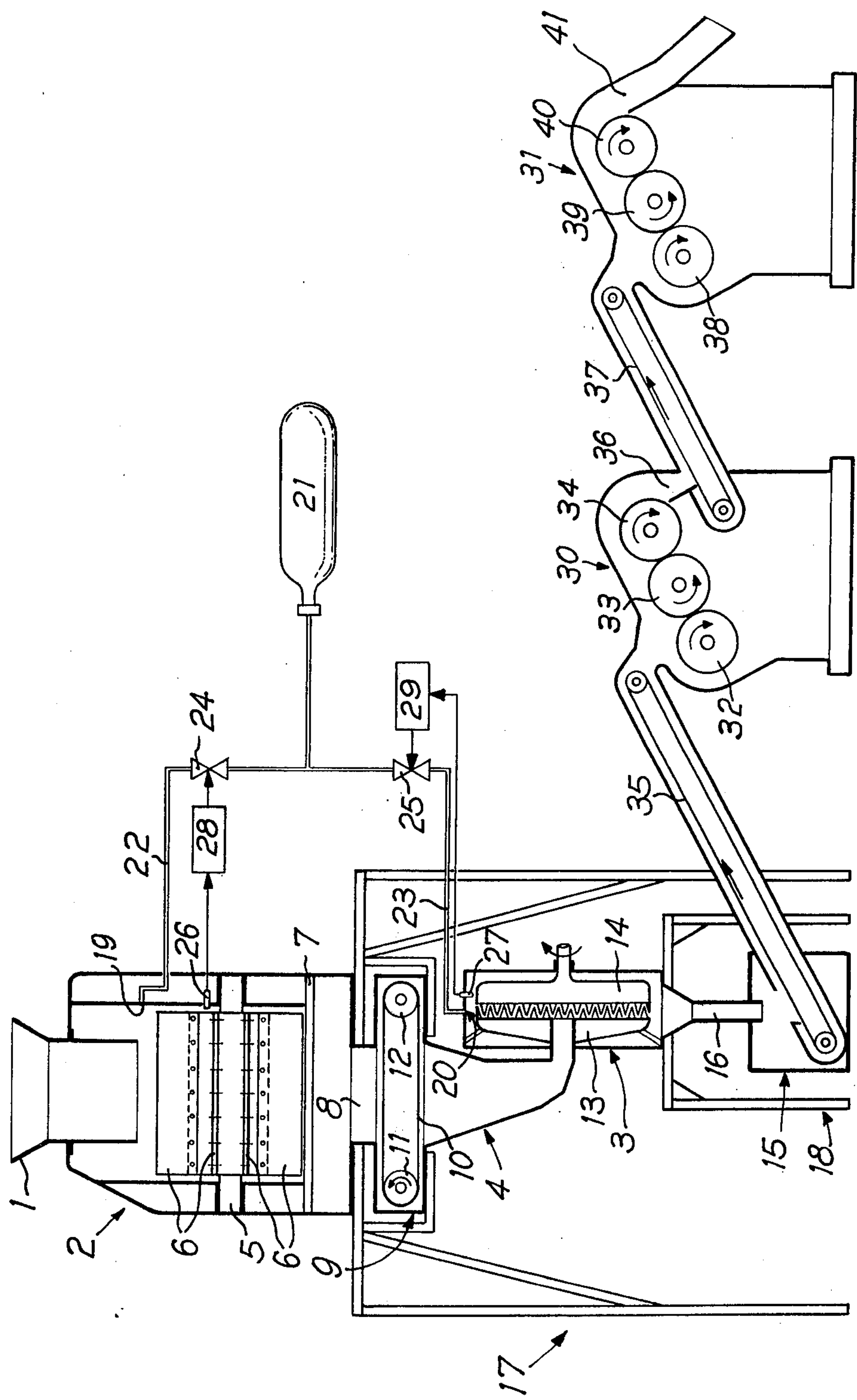
1
2
19
26
22
28
24
21
29
25
23
27
14
7
8
12
11
20
13
3
16
15
18
10
4
6
5
6
9
17
35
32
33
30
34
36
37
38
39
31
40
41

METHOD AND APPARATUS FOR COMMUNITING MARINE ALGAE AND THE RESULTING PRODUCT

BACKGROUND OF THE INVENTION

The present invention relates to a method and apparatus for comminuting marine algae and to the resulting product.

In a broken-down state, green and brown marine algae are capable of many applications, in particular in the field of agriculture, due to the active substances which they contain, among which are, in particular, vitamins and phytohormones. Known processes for comminuting, i.e. reducing the particle size of performed algae, are performed at ambient temperature with algae which have previously been dried in the atmosphere or dehydrated with hot air, or both, which has the serious disadvantage that it destroys a large proportion of the active substances contained in the algae.

The present invention has as an object to overcome this disadvantage and to provide a method of and an apparatus for comminuting algae by means of which it is possible to obtain an algae mix which is rich in active substances.

SUMMARY OF THE INVENTION

Accordingly, the invention consists in a method of comminuting fresh algae, which consists in carrying out a comminuting operation on said algae at a temperature lower than 20° C.

Preferably the comminuting temperature lies within the range between 30° and 100° C. It is advantageous for the fresh algae to be frozen before being comminuted at a temperature of less than 20° C.

In accordance with a feature of the method according to the invention, the broken down algae are comminuted by crushing to the form of a wet paste-mix, the particles contained in which mix are of a mean size less than 100 micrometers and preferably less than 50 micrometers.

The invention also consists in a comminutor, i.e. comminuting apparatus, which comprises a comminuting assembly and means to maintain the temperature within said assembly at a level lower than −20° C, and preferably one between −30° and −100° C, by means of a cooling agent.

In accordance with a feature of the apparatus according to the invention, the apparatus also includes at least one roller reducer into which the matter emerging from the first reducing i.e. comminuting assembly is able to be fed.

The fact that the comminuting assembly is cooled, on the one hand prevents the algae from warming up in a disadvantageous way and, on the other hand, enables the frozen algae to be reduced efficiently, the algae being broken down into fragments. The fact that the fresh algae are frozen beforehand enables a saving to be made of cooling agent during the actual comminuting operation. Advantageously, the broken down algae are crushed to produce a wet paste-mix the particles in which are sufficiently small in size to enable it to be used in sprayers.

BRIEF DESCRIPTION OF THE DRAWING

Other features and advantages of the method and apparatus according to the invention will become apparent from perusal of the following description of a particular embodiment thereof, which is given by way of non-limiting illustration with reference to the accompanying drawing comprising one FIGURE, which is a schematic view of a comminuting apparatus according to the invention.

DETAILED DESCRIPTION OF A PREFERRED EMBODIMENT

Referring now to the drawing, the algae intended for comminution are frozen when freshly cut up at a temperature of less than −20° C, one between −20° C and −50° C for example. The frozen algae are fed by means of a supply hopper 1 into a comminuting assembly which consists of a bladed comminutor 2 and a toothed comminutor 3 which are connected by a passage 4.

The bladed comminutor 2 includes a shaft 5 which carries knives or blades 6 and which is driven round by any desired known means (which are not shown), and a fixed bar 7 which is adjacent the path followed by the ends of the blades and may possibly itself be provided with a blade. After having been shredded, the algae are discharged from the lower part of the bladed comminutor 2 via a passage 8 and pass onto a feeder 9. Feeder 9 is formed by a continuous horizontal belt 10 which runs on a drive pulley 11, which is driven by a motor, which is not shown, and a return pulley 12. Feeder 9 supplies the toothed comminutor 3 via a passage 4 in the form of a funnel. The toothed comminutor 3 includes a coaxial stator 13 and rotor 14 the axes of which are horizontal. The stator 13 contains an axial opening and the algae which pass through this opening are broken down between the stator 13 and the rotor 14 by means of the teeth with which the opposing faces of the stator and rotor are provided, the ends of the teeth on the stator projecting between the ends of the teeth on the rotor and vice versa. The rotor 14 is driven by a any convenient known motor (not shown) at a speed of the order of 8,000 revolutions per minute. In leaving the toothed comminutor 3, the ground algae are expelled from the gap between the stator 13 and rotor 14 and are deposited in a second hopper 15 via a passage 16.

The bladed comminutor 2 is located at a higher level than the toothed comminutor 3 and rests on a framework 17 which also supports the feeder 9. The comminutor 3 is arranged above hopper 15 and is supported by a framework 18.

In order that the frozen algae may be comminuted efficiently, the comminutor assembly is held at a temperature of less than −20° C. To this end, the working areas of the comminutors 2 and 3 are cooled by a cooling agent. For this purpose, injection ports such as 19 and 20, which may for example be so arranged as to form banks of ports, open onto the working areas of the bladed and toothed comminutors respectively and are connected to a source of cooling agent, such as a container 21 of liquid nitrogen, by means of pipes 22 and 23. The flow of liquid nitrogen through pipes 22 and 23 is controlled by regulator valves 24 and 25 respectively. So that the temperature in the working areas of the bladed and toothed comminutors can be maintained at a desired level, at least one temperature probe such as 26 or 27 respectively, is arranged in each of the said areas and is connected to a member 28 and 29 respectively, for controlling the regulator valves 24 and 25. Control members 28 and 29 may be adjusted to suit the temperature required in the working areas of the comminutors. This temperature will preferably be between −30° C and −100° C, and may for example be close to −50° C, with the object on the one hand of maintaining the temperature of the algae within the assembly formed by comminutors 2 and 3 and passage 4 at a level below −20° C, so that the algae will remain frozen, and on the other hand to avoid too great a consumption of liquid nitrogen.

Cooling by injecting liquid nitrogen has proved to be effective due to the evaporation of the liquid nitrogen as it emerges from the injection ports. It is however also possible for the cooling to be carried out by circulating liquid nitrogen through pipes arranged in or near the walls of the respective working areas of comminutors 2 and 3, and in this case the flow of liquid nitrogen through the pipes may be controlled by a regulating arrangement which consists of at least one temperature sensor, one control member and one regulating valve as described above. In addition, it has proved preferable for the walls of comminutors 2 and 3, for example, to be thermally insulated by covering them on the outside with insulating materials such as polyurethanes, polyesters, etc.

In the form in which they are received in hopper 15, the fragments of broken-down algae have a mean size of the order of 0.1 to 0.5 millimeters and are thus too large to be used subsequently in sprayers. It is therefore advantageous for the broken-down algae to be fed on to one or more further size reducers, such as triple roller reducers similar to 30 and 31, in order to reduce this mean size to less than 100 micrometers and preferably to 50 micrometers.

The first roller size reducer 30 has, in a known way, three rollers 32, 33 and 34 whose axes are mutually parallel, with the roughing-down roller 32 and the collecting roller 34 pressing on either side against the center roller 33 and both turning in the same direction, which is opposite from that of roller 33. The broken-down algae coming from the comminuting assembly which are deposited in hopper 15 are fed onto a conveyor belt 35 which drops them between the roughing-down roller 32 and the center roller 33. The algae are successively crushed between rollers 32 and 33 and 33 and 34 and are tipped from roller 34 into the output 36 from roller reducer 30. The matter coming from roller reducer 30 is fed on by an endless conveyor belt 37 to the input of the second triple-roller reducer 31. The latter is similar in structure and operation to reducer 30 and has three rollers 38, 39 and 40 which are roughing-down center and collecting rollers respectively. The algae crushed between rollers 38, 39 and 40 are collected at the output 41 of reducer 31. Conveyor belts 35 and 37 and reducers 30 and 31 are driven by means which are not shown.

Advantageously, the roughing-down and collecting rollers 30 and 31 are made slightly convex in outline while the center roller is straight sided. Preferably the camber of the roughing-down roller is between one and eight hundredths of a millimeter, and preferably between two and four hundredths of a millimeter, that is to say that the radius of the roller at the center is greater by one to eight hundredths of a millimeter, and preferably by two to four hundredths of a millimeter, than the radius at the ends of the roller. The collecting roller has a camber of between nought and five hundredths of a millimeter and preferably 1 and three hundredths of a millimeter. When the camber of the rollers is within the limits quoted above, this allows the matter to pass between them satisfactorily. The pieces of algae coming from the first comminutor assembly warm up in hopper 15, where they may be left to wait for some time. The phase of crushing by means of the roller reducers takes place at ambient temperature, the temperature of the broken down and crushed algae changing from approximately −10° C to + 15° C, which enables a wet paste-mix to be obtained at output 41. This paste contains particles the size of which is less than 100 micrometers and on average is between 10 and 50 micrometers. The rollers of each of the roller reducers are preferably driven at the highest possible speed in order to obtain maximum output at outlet 41.

The use of two triple roller reducers, the bodies of the rollers of which are 1 meter long in the case of the first reducer and 1.3 meters long in the case of the second reducer, with a diameter of 0.4 meters, and of which the roughing-down rollers have a camber of three hundredths of a millimeter and the collecting rollers a camber of one hundredth of a millimeter, allows a paste to be obtained the particles in which have a mean size of 20 micrometers.

The method and apparatus which have just been described are used on green and brown marine algae collected at sea, which may for example, be stored, after being cut up, on a boat having a fresh-storage well. The brown and green algae which are taken belong to the classes of pheophyceae and chlorophyceae and are such as the laminariae (laminaria flexicaulis for example) the fuci (fucus spiralis for example) and the ascophyllal (ascophyllum modosum for example) and other related types.

Once landed, the algae are preferably stored in cold chambers to allow them to be frozen, which on the one hand allows them to be kept fresh and on the other prevents the excessive consumption of liquid nitrogen which would be required if fresh algae were fed into the comminutor assembly without having first been frozen.

The raw product obtained by means of the method or apparatus described above takes the form of a thick green paste the pH of which is approximately 4.8, which is stable under normal storage conditions at ambient temperature and which can be mixed with water simply by stirring. The product contains in particular clorophyll; algin, and laminarin, the combined content of which by weight is equal to approximately 15 to 20% of the weight of dry solids and it also contains phytohormones, in particular gibberillins, amino-acids, and elements such as sulphur, magnesium, iodine and other trace elements.

It will be noted that when the fresh algae are comminuted when cold, all the substances which were originally contained in the algae can be found in the end product whereas known methods, in which the algae are dried in the open air and/or are dehydrated with hot air before comminution and after being washed in soft water, have the drawback that they cause the irreparable loss of some or all of the vitamins and phytohormones at temperatures above 60° C and that of the laminarin and algin.

Table I below gives, by way of illustration, the amounts of the various constituents found in a raw product according to the invention, the amounts being given in relation to the weight of the raw product. The amounts may vary with the time of collection and the relative proportions of the types of algae involved.

Table I

| | | | | |
|---|---|---|---|---|
| Total nitrogen | from | 4.50 | to | 5.50% |

Table I-continued

| | | | | |
|---|---|---|---|---|
| Ammoniacal nitrogen | " | 0.55 | " | 0.65% |
| Nitric nitrogen | " | 0.90 | " | 1.00% |
| Ureic nitrogen | " | 2.45 | " | 3.00% |
| Organic nitrogen | " | 0.55 | " | 0.80% |
| Total sulphur (expressed as S) | " | 0.20 | " | 0.40% |
| Sulphates (expressed as S) | " | 0.10 | " | 0.17% |
| Iodine | " | 170.00 | " | 250 mg/kg |
| Iron | " | 310 | " | 460 mg/kg |
| Magnesium | " | 800 | " | 1200 mg/kg |
| Copper | " | 20 | " | 35 mg/kg |
| Carotene (provitamin A) | " | 1 | " | 1.50 mg/kg |
| Vitamin C | " | 90 | " | 130 mg/kg |
| Vitamin B 12 | " | 2.75 | " | 4.25 micro-grammes/kg |
| Total phosphoric acid | " | 3.90 | " | 4.80% |
| Potassium | " | 2.70 | " | 3.35% |
| Weight of dry solids | " | 27 | " | 30.00% |

The raw material produced by practicing the invention is able to be used in the agricultural field and may be employed as a growth promoting substance for plants, in particular by spraying a composition which contains it in solution or suspension in water onto the plants. Its growth-promoting effect on plants is illustrated by the results of trials which are given, by way of illustration, in Tables II, III, IV, V and VI below. It can be seen from Table I that the product according to the invention contains insufficient quantities of nitrogen and potassium to allow it to be considered as a leaf fertiliser. It is however possible for the product to be used with advantage in combination with leaf fertilisers and similar products.

Table II gives the results of comparative trials carried out on three plots of land A, B, C which were planted with "UGNI BLANC" varieties of COGNAC vine, plots A, B and C being respectively a control plot, a plot which was treated by spreading with five 15 kg/hectare applications of leaf fertiliser, and a plot which was treated by spraying with four 12 kg/hectare applications of the raw product according to the invention with water added.

TABLE II

| | A | B | C |
|---|---|---|---|
| Hectolitres of wine per hectare | 132.2 | 151.7 | 167.1 |
| Proportional yields of pure alcohol per hectare | 100 | 103 | 119 |

It was noted that the vines on plot C showed considerably less coulure and shot berries and that their fruit developed better, which explains the greater quantitative and alcohol yields from the plants treated with the product made according to the invention.

Table III gives the results of comparative trials carried out on two plots A and B planted with apple trees of the "GOLDEN" variety, plot A being a control plot and plot B having been treated by spraying with four 12 kg/hectare applications of the product according to the invention with water added.

TABLE III

| | Size of fruit picked in mm. | | | | | |
|---|---|---|---|---|---|---|
| | :60 : | 60/65 : | 65/70 : | 70/75 : | 75/80 : | 80 |
| A Percentage of fruit picked by size | 12.50 : | : | 22.50 : | 13.05 : | 1.20 : | 0.75 |
| | | | | 36.75 | | |
| B " | 0.96 : | 16.90 ; | 18.10 : | 37.50 : | 17.87 : | 8.67 |
| | | | | 73.47 | | |

These results show that the fruit picked from trees which had been treated with a product according to the invention were larger and more uniform in size.

Table IV gives the results of comparative trials carried out on two plots A and B planted with strawberry plants of the "TIOGA" variety and two plots C and D which were planted with strawberry plants of the "ALISO" variety, plots A and C being control plots and plots B and D being sprayed with three 12 kg/hectare applications of raw product according to the invention with water added.

TABLE IV

| Time of picking | Amount picked in kg/hectare A | B | C | D |
|---|---|---|---|---|
| 15 to 31 March | 1.124 | 1,712 | 888 | 2,313 |
| 1 to 15 April | 2,461 | 2,676 | 2.688 | 3,250 |
| 16 to 30 April | 1,765 | 1,765 | 1,625 | 1,875 |
| TOTAL | 5,350 | 6,153 | 5,201 | 7,438 |

These results demonstrate the better yields and the earlier fruiting of the strawberry plants treated in accordance with the invention.

Table V gives the results of comparative trials carried out on plots A, B and C which were planted with potatoes of the "SIRTENA" variety, with plot A being a control plot, plot B being sprayed with 3 kg/hectare of product according to the invention before the potatoes were earthed up, and plot B being sprayed with 7 kg/hectare of product, consisting of 3.5 kg/hectare before earthing up and 3.5 kg/hectare before flowering.

TABLE V

| | A | B | C |
|---|---|---|---|
| Proportional yield per hectare | 100 | 129 | 137 |
| Percentage of potatoes gathered larger than 28 mm in size | 85.5% | 90% | 92.7% |

These results show an increase in yield and size for potatoes on the plots treated with a product according to the invention.

Finally, Table VI shows the results of comparative tests carried out on greenhouse-grown lettuces, lettuces A being the controls, lettuces B being treated with a leaf fertilizer under the normal conditions, and lettuces C being treated with a product according to the invention with added water, the quantity of raw product used being equivalent to 12 kg/hectare.

TABLE VI

| | A | B | C |
|---|---|---|---|
| Dry weight of 3 lettuces (grams) | 16.5 | 16 | 18.5 |
| Chlorophyll A (in mg per 100 g of fresh matter) | 0.401 | 0.401 | 0.487 |
| Chlorophyll B (in mg per 100 g of fresh matter) | 0.240 | 0.245 | 0.282 |
| Carotene (provitamin A) (in mg per 100 g of fresh matter) | 0.278 | 0.272 | 0.419 |

These results show the effect of the product according to the invention on the chlorophyll and carotene contents. The result of the increase in these contents is that the lettuces develop earlier and to a greater extent, which is confirmed by the measurements of dry weight.

It is clear from the trials which were carried out that the product according to the invention has a substantial effect when used, possibly over a number of applications, in a total amount approximately equal to at least 3.5 kg/hectare and preferably equal to an average of between 7.5 and 15 kg of raw product (i.e. between 2.2 and 4.5 kg of dry product) per hectare. The addition of water is necessary so that the product can be sprayed over a large area.

We claim:

1. The method for producing algae pulp, the mean size of the particles in which is less than 100 micrometers, comprising:

freezing fresh algae at a temperature of less than −20° C;

feeding said frozen algae into a comminuting assembly;

comminuting said frozen algae while maintaining within said comminuting assembly a temperature lying within the range −30° to −100° C;

continuously feeding the solid fragments of comminuted algae obtained at the output of said comminuting assembly into roller size reducer means; and crushing said fragments at ambient temperature whereby said fragments are crushed and warmed up to obtain said algae pulp at the output of said roller size reducer means.

2. The method as set forth in claim 1, which includes feeding said frozen algae into a bladed comminutor and continuously feeding the pieces of frozen algae obtained at the output of said bladed comminutor into a toothed comminutor to obtain said solid fragments of frozen algae at the output of said toothed comminutor.

3. The method as set forth in claim 1, which includes feeding said solid fragments of comminuted algae into at least one roller size reducer comprising a roughing-down roller, a centre roller and a collecting roller, said rollers having mutually parallel axes, said roughing-down and collecting rollers pressing on either side against said center roller and both rotating in a same direction opposite that of the center roller, and said roughing-down and collecting rollers each having a convex outline with a camber of between 1 and 8/100 of a millimeter in the case of the roughing-down roller and a camber of between 0 and 5/100 of a millimeter in the case of the collecting roller while said centre roller is straight-sided.

4. The method as set forth in claim 1, which includes cooling the interior of said comminuting assembly by evaporating liquid nitrogen injected thereinto through at least one injection port and controlling the flow of injected liquid nitrogen.

5. The method as set forth in claim 1, which includes cooling the interior of said comminuting assembly by controlling the flow of liquid nitrogen flowing through a cooling circuit.

* * * * *